United States Patent
Cid-Núñez

(10) Patent No.: US 10,138,237 B2
(45) Date of Patent: Nov. 27, 2018

(54) 1,2,4-TRIAZOLO[4,3-A]PYRIDINE COMPOUNDS AND THEIR USE AS POSITIVE ALLOSTERIC MODULATORS OF MGLUR2 RECEPTORS

(71) Applicant: Janssen Pharmaceutica NV, Beerse (BE)

(72) Inventor: José Maria Cid-Núñez, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/533,798

(22) PCT Filed: Dec. 10, 2015

(86) PCT No.: PCT/EP2015/079216
§ 371 (c)(1),
(2) Date: Jun. 7, 2017

(87) PCT Pub. No.: WO2016/092002
PCT Pub. Date: Jun. 16, 2016

(65) Prior Publication Data
US 2017/0362222 A1   Dec. 21, 2017

(30) Foreign Application Priority Data
Dec. 11, 2014 (EP) .................... 14197277

(51) Int. Cl.
*C07D 471/04* (2006.01)
(52) U.S. Cl.
CPC .................... *C07D 471/04* (2013.01)
(58) Field of Classification Search
CPC .................... C07D 471/04
See application file for complete search history.

(56) References Cited

U.S. PATENT DOCUMENTS

| 8,716,480 | B2 * | 5/2014 | Cid-Nunez | ........... | C07D 471/04 |
| | | | | | 546/119 |
| 8,937,060 | B2 * | 1/2015 | Cid-Nunez | ........... | C07D 471/04 |
| | | | | | 514/210.21 |
| 8,946,205 | B2 * | 2/2015 | Cid-Nunez | ........... | C07D 471/04 |
| | | | | | 514/211.09 |
| 8,993,591 | B2 * | 3/2015 | Cid-N Nez | ........... | A61K 31/542 |
| | | | | | 514/303 |
| 9,012,448 | B2 * | 4/2015 | Cid-N Nez | ........... | A61K 9/0019 |
| | | | | | 514/233.2 |
| 9,271,967 | B2 * | 3/2016 | Cid-N Nez | ............ | A61K 45/06 |
| 9,708,315 | B2 * | 7/2017 | Cid-N nez | ........... | C07D 471/04 |

FOREIGN PATENT DOCUMENTS

| WO | 2010130422 A1 | 11/2010 |
| WO | 2010130423 A1 | 11/2010 |
| WO | 2010130424    | 11/2010 |
| WO | 2012062750 A1 | 5/2012 |
| WO | 2012062751 A1 | 5/2012 |
| WO | 2012062752 A1 | 5/2012 |

OTHER PUBLICATIONS

International Search Report re: PCT/EP2015/079216 dated Feb. 25, 2016.
International Search Report re: PCT/EP2015/078285 dated Feb. 1, 2016.
International Search Report re: PCT/EP2015/078296 dated Feb. 19, 2016.
A.-M. Linden et al, Comparison of c-Fos induction in the brain by the mGlu2/3 receptor antagonist LY341495 and agonist LY354740: Evidence for widespread endogenous tone at brain mGlu2/3 receptors in vivo, Neuropharmacology, May 5, 2005, pp. 120-134, vol. 49.
Ahnaou et al, Modulation of group II metabotropic glutamate receptor (mGlu2) elicits common changes in rat and mice sleep—wake architecture, European Journal of Pharmacology, Nov. 17, 2008, pp. 62-72, vol. 603.
Alfonso R Gennaro, 18th edition Remington's—Pharmaceutical Sciences, 18th edition Remington's—Pharmaceutical Sciences, 1990, Part 8_ Pharmaceutical preparations and their Manufacture_ pp. 1435-1714, Part 8.
Anantha Shekhar et al, Panic disorder and agoraphobia: Novel glutamate mechanisms and therapeutic approaches from preclinical model, ACNP 52nd Annual Conference, 2013, S582-S583, article No. W220.
Bruce J. Kinon et al, A Multicenter, Inpatient, Phase 2, Double-BLind, Placebo-Controlled Dose-Ranging Study of LY2140023 Monohydrate in Patients With DSM-IV Schizophrenia, J.of Clinical Psychopharmacology, 2011, pp. 349-355, vol. 31, No. 3.
Carrie K. Jones et al, Analgesic effects of the selective group II (mGlu2/3) metabotropic glutamate receptor agonists LY379268 and LY389795 in persistent and inflammatory models after acute and repeated dosing, Neuropharmacology, May 5, 2005, pp. 206-218, vol. 49.
D. Michelson et al, Clinical studies with mGluR2/3 agonists: LY354740 compared with placebo in patients with generalized anxiety disorder, Abstracts/Neuropharmacology, 2005, pp. 257, 49.
David H. Adams et al, A long-term, phase 2, multicenter, randomized, open-label, comparative safety study of pomaglumetad methionil (LY2140023 monohydrate) versus atypical antipsychotic standard of care in patients with schizophrenia, BMC Psychiatry, 2013, pp. 143, 13.
Dunayevich et al, Efficacy and tolerability of an mGlu2/3 agonist in the treatment of generalized anxiety disorder, Neuropsychopharmacology, 2008, pp. 1603-1610, vol. 33(7).
Dyatkin et al, Determination of the Absolute Configuration of a Key Tricyclic Component of a Novel Vasopressin Receptor Antagonist by Use of Vibrational Circular Dichroism, Chirality, 2002, pp. 215-219, vol. 14.

(Continued)

*Primary Examiner* — Golam M Shameem

(57) ABSTRACT

The present invention relates to novel 1,2,4-triazolo[4,3-a] pyridine compounds as positive allosteric modulators (PAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which mGluR2 subtype of metabotropic receptors is involved.

5 Claims, No Drawings

(56) References Cited

OTHER PUBLICATIONS

Finney, Probit Analysis, 34d Ed 1971, London: Cambridge University Press.
Galici et al, A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, The Journal of Pharmacology and Experimental Therapeutics, 2005, pp. 1181-1187, vol. 315.
Govek et al, Benzazoles as allosteric potentiators of metabotropic glutamate receptor 2 (mGluR2): Efficacy in an animal model for schizophrenia, Bioorganic & Medicinal Chemistry Letters, 2005, pp. 4068-4072, vol. 15.
H. Steve White et al, General Principles: Experimental Selection, Quantification, and Evaluation of Antiepileptic Drugs, Antiepeleptic Drugs, Fourth Edition, 1995, pp. 99-110, chapter 7, Raven Press, Ltd, New York.
J. Konieczny et al, LY354740, a group II metabotropic glutamate receptor agonist with potential antiparkinsonian properties in rats, Naunyn-Schmiedebergs Arch.Pharmacology, Jul. 21, 1998, pp. 500-502, vol. 358.
James E. Barrett, mGluR2-Positive Allosteric Modulators: Therapeutic Potential for Treating Cocaine Abuse?, Neuropsychopharmacology, Jun. 7, 2010, pp. 2007-2008, vol. 35.
Johnson et al, Discovery of Allosteric Potentiators for the Metabotropic Glutamate 2 Receptor: Synthesis and Subtype Selectivity of N-(4-(2-Methoxyphenoxy)phenyl)-N-(2,2,2-trifluoroethylsulfonyl)pyrid-3-ylmethylamine, Journal of Medicinal Chemistry, 2003, pp. 3189-3192, vol. 46.
Johson et al, Metabotropic glutamate 2 receptor potentiators: receptor modulation, frequency-dependent synaptic activity, and efficacy in preclinical anxiety and psychosis model(s), Psychopharmacology, 2005, pp. 271-283, vol. 179.
Kari A. Johnson et al, Glutamate Receptors as Therapeutic Targets for Parkinson's Disease, CNS & Neurological Disorders—Drug Targets, 2009, pp. 475-491, vol. 8.
Larock et al, -, Comprehensive Organic Transformations, 1989, pp. 595-596.
M.Foster Olive, Metabotropic Glutamate Receptor Ligands as Potential Therapeutics for Addiction, Current Drug Abuse Reviews, 2009, pp. 83-98, vol. 2.
Matthew E. Barton et al, Comparison of the effect of glutamate receptor modulators in the 6 Hz and maximal electroshock seizure models, Epilepsy Research, Aug. 4, 2003, pp. 17-26, vol. 56.
Moldrich et al, Glutamate metabotropic receptors as targets for drug therapy in epilepsy, European Journal of Pharmacology, 2003, p. 3-16, vol. 476.
Peter De Boer et al, Characterization of the Clinical Effect of a Positive Allosteric Modulator of the Metabotropic Glutamate Receptor-2, Society of Biological Psychiatry 67th annual Scientific Convention & Program May 3-5, 2012, PA, US, Dec. 15, 2012, 2013-P-1060-SOBP, Poster Abstract.
Robert E. Litman, AZD8529, A positive Allosteric Modulator at the mGluR2 Receptor, Does not Improve Symptoms in Schizophrenia: A proof of Principle Study, Poster& Abstract NCDEU meeting, 2013, 1-3, na.
Sandeep T. Patil et al, Activation of mGlu2/3 receptors as a new approach to treat schizophrenia: a randomized Phase 2 clinical trial, Nature Medicine—Letters, 2007, pp. 1102-1107, vol. 13 No. 9.
Santina Chiechio et al, Metabotropic glutamate receptors and the control of chronic pain, Current Opinion in Pharmacology, Oct. 29, 2011, pp. 28-34, vol. 12.
Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.
Schiefer et al, The metabotropic glutamate receptor 5 antagonist MPEP and the mGluR2 agonist LY379268 modify disease progression in a transgenic mouse model of Huntington's disease, Brain Research, 2004, pp. 246-254, vol. 1019.
Simmons et al, Group II mGluR receptor agonists are effective in persistent and neuropathic pain models in rats, Pharmacology, Biochemistry and Behavior, 2002, pp. 419-427, vol. 73.
Volker Neugebauer, Metabotropic glutamate receptors—important modulators of nociception and pain behavior, Pain, May 9, 2002, pp. 1-8, vol. 98.

\* cited by examiner

1,2,4-TRIAZOLO[4,3-A]PYRIDINE COMPOUNDS AND THEIR USE AS POSITIVE ALLOSTERIC MODULATORS OF MGLUR2 RECEPTORS

CROSS REFERENCE TO RELATED APPLICATIONS

This application is the national stage of PCT Application No. PCT/EP2015/079216, filed Dec. 10, 2015, which claims priority from European Patent Application No. 14197277.8, filed Dec. 11, 2014, the entire disclosures of which are hereby incorporated in their entirety.

FIELD OF THE INVENTION

The present invention relates to novel 1,2,4-triazolo[4,3-a]pyridine compounds as positive allosteric modulators (PAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which mGluR2 subtype of metabotropic receptors is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptor channels (iGluRs), and the NMDA, AMPA and kainate receptors which are responsible for fast excitatory transmission.

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signaling pathways.

The mGluR2 subtype is negatively coupled to adenylate cyclase via activation of Gαi-protein, and its activation leads to inhibition of glutamate release in the synapse. In the central nervous system (CNS), mGlu2 receptors are abundant mainly throughout cortex, thalamic regions, accessory olfactory bulb, hippocampus, amygdala, caudate-putamen and nucleus accumbens.

Activating mGluR2 was shown in clinical trials to be efficacious to treat anxiety disorders (for studies with orthosteric mGlu2/3 agonists, see Michelson et al. Neuropharmacology 2005, 49(S1), 84-257; Dunayevich et al. Neuropsychopharmacology 2008, 33(7), 1603-10), LY354740 had been previously evaluated in non-clinical and clinical model systems predicting utility in the treatment of anxiety disorders beyond generalized anxiety depression (GAD), e.g. panic (see Dunayevich et al. 2008). Non-clinical studies, suggest a role for both mGlu2 and mGlu3 receptors in anxiolysis (Linden et al. Neuropharmacology 2005, 49, 120-134) whilst it has been suggested that positive allosteric modulation of the mGluR2 may be sufficient for an anxiolytic effect (Johnson et al. Psychopharmacology (Berl) 2005, 179(1), 271-283).

In addition, activating mGluR2 was shown to be potentially efficacious for the treatment of (a) schizophrenia (Patil et al. Nat Med 2007, 13(9), 1102-7); later studies however, do not support treatment of acute exacerbations of schizophrenia with an mGluR2 agonist or allosteric modulator (Adams et al. BMC Psychiatry 2013, 13(1), 143; Kinon et al. J Clin Psychopharmacol. 2013, 31(3), 349-55; Litman et al. (2013) NCDEU Meeting (abstract)) but do not exclude application for other specific symptom clusters (e.g. negative symptoms (Kent et al. "Safety, tolerability and potential therapeutic efficacy of a novel glutamate modulator as adjunctive treatment in patients with schizophrenia" abstract No. 3160 and poster NR10-47, American Psychiatric Association 166th Annual Meeting 2013 (APA 2013), May 18-22, 2013, San Francisco, Calif., USA)) or for other phases in the disease (e.g. residual symptoms);

(b) epilepsy, based on acute non-clinical studies with mixed mGlu2/3 receptor agonists (Moldrich et al. Eur J Pharmacol. 2003, 476, 3-16; Barton et al. Epilepsy Research 2003, 56, 17-26); continued administration of an mGlu2/3 agonist paradoxically induced seizure activity in long-term toxicology studies (Dunayevich et al. (2008), this paradoxical effect may be related to agonist-induced changes in the sensitivity of the receptor systems (tachyphylaxis); positive allosteric modulators, in contrast, modulate ongoing neurotransmission but are not directly stimulatory, thereby reducing the risk for tachyphylaxis;

(c) drug addiction/dependence (Barrett, Neuropsychopharmacology 2010, 35, 2007-2008; Foster, Curr Drug Abuse Rev 2009, 2, 83-98);

(d) Parkinson's disease (see for example Johnson et al. CNS Neurol Disord Drug Targets 2009, 8, 475-491; Konieczny et al. Naunyn Schmiedebergs Arch. Pharmacol. 1998, 358 (4), 500-502);

(e) pain (Chiechio and Nicoletti, Curr Opin Pharmacol 2012, 12, 28-34; Jones et al. Neuropharmacology 2005, 49, 206-218; Neugebauer, [Review] Pain 2002, 98 (1-2), 1-8; Simmons et al. Pharmacology, Biochemistry and Behavior 2002, 73, 419-427);

(f) sleep disorders (Ahnaou et al. European Journal of Pharmacology 2009, 603, 62-72);

(f) Huntington's disease (based on a potential disease modifying effect (Schiefer et al. Brain Res 2004, 1019, 246-254) which is to be confirmed further); and (g) depression (although no efficacy signal was detected on the primary outcome measure, adjunctive administration of JNJ-40411813/ADX71149 in the dose range tested in a multicenter, double-blind, placebo-controlled study in adults with major depressive disorder with anxiety symptoms showed efficacy signals on several secondary outcome measures of both depression and anxiety (Kent et al. "Efficacy and Safety of a Novel mGlu2 Receptor Positive Allosteric Modulator as an Adjunctive Treatment to an SSRI/SNRT in the Treatment of Anxious Depression", Abstract to poster and oral presentation, American Society of Clinical Psychopharmacology (ASCP) 2014 Annual Meeting, Jun. 16-19, 2014 Westin Diplomat, Hollywood, Fla.)).

A new avenue for developing selective compounds acting at mGluRs is to identify compounds that act through allosteric mechanisms, modulating the receptor by binding to a site different from the highly conserved orthosteric binding site.

Positive allosteric modulators of mGluRs have emerged recently as novel pharmacological entities offering this attractive alternative.

It was demonstrated that such compounds do not activate the receptor by themselves. Rather, they enable the receptor to produce an increased response to a concentration of glutamate, which by itself induces a minimal response. Mutational analysis has demonstrated unequivocally that the binding of mGluR2 positive allosteric modulators does not occur at the orthosteric site, but instead at an allosteric site situated within the seven transmembrane region of the receptor.

Animal data suggest that positive allosteric modulators of mGluR2 have effects in anxiety and psychosis models similar to those obtained with orthosteric agonists. Allosteric modulators of mGluR2 were shown to be active in fear-potentiated startle (Johnson et al. J Med Chem 2003, 46, 3189-3192; Johnson et al. Psychopharmacology 2005, 179, 271-283), and in stress-induced hyperthermia models of anxiety (Johnson et al. 2005). Furthermore, such compounds were shown to be active in reversal of ketamine—(Govek et al. Bioorg Med Chem Lett 2005, 15(18), 4058-4072) or amphetamine—(Galici et al. J Pharm Exp Ther 2005, 315 (3), 1181-1187) induced hyperlocomotion, and in reversal of amphetamine-induced disruption of prepulse inhibition of the acoustic startle effect (Galici et al. 2005) models of schizophrenia.

JNJ-40411813/ADX71149, an mGlu2 PAM (which in rat also displays 5-HT$_{2A}$ antagonism activity due to a rat-specific metabolite) has undergone clinical trials for the treatment of schizophrenia, and anxiety-depression (see for instance www.Clinicaltrials.gov). Non-clinical data in the lactate-induced panic model in rodents suggests that it could have potential in the treatment of further anxiety disorders such as panic disorder and phobias, such as agoraphobia (Shekhar et al. Neuropsychopharmacology 2013, 38, S435-S593 (W220). JNJ-40411813 was also observed to reduce craving and improve smoking cessation-induced deficits in attention and episodic memory versus placebo (Salih et al. Journal of Psychopharmacology, submitted) and showed an efficacy signal in S-ketamine-induced negative symptoms in healthy volunteers and patients with predominant negative symptoms of schizophrenia (De Boer et al. Society of Biological Psychiatry 68th Annual Scientific Convention of Society of Biological Psychiatry, May 16-18, 2013, Hilton Union Square, San Francisco, Calif., Abstract 2013-P-1060-SOBP).

Positive allosteric modulators enable potentiation of the glutamate response, but they have also been shown to potentiate the response to orthosteric mGluR2 agonists such as LY379268 or DCG-IV. These data provide evidence for yet another novel therapeutic approach to treat the above mentioned neurological and psychiatric diseases involving mGluR2, which would use a combination of a positive allosteric modulator of mGluR2 together with an orthosteric agonist of mGluR2.

Various compounds have been described as mGluR2 positive allosteric modulators. WO2010/130424, WO2010/130423, WO2010/130422, and WO2012/062750, WO2012/062751, and WO2012/062759, published on 18 Nov. 2010 and 18 May 2012, respectively, disclose 1,2,4-triazolo[4,3-a]pyridine derivatives as mGluR2 positive allosteric modulators.

DETAILED DESCRIPTION OF THE INVENTION

The present invention is directed to 1,2,4-triazolo[4,3-a]pyridine derivatives of Formula (I)

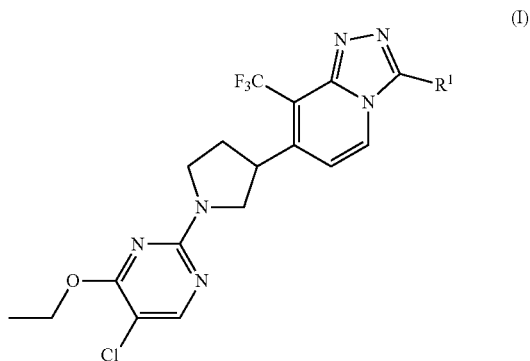

and the stereochemically isomeric forms thereof, wherein
R$^1$ is selected from C$_{1-6}$alkyl, (C$_{3-8}$cycloalkyl)C$_{1-3}$alkyl, and (C$_{1-3}$alkyloxy)C$_{1-3}$alkyl;
and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament and to a compound of Formula (I) for use as a medicament for the treatment or prevention of neurological and psychiatric disorders in which mGluR2 is involved.

The invention also relates to the use of a compound according to Formula (I) or a pharmaceutical composition according to the invention for the manufacture of a medicament for treating or preventing neurological and psychiatric disorders in which mGluR2 is involved.

Additionally, the invention relates to the use of a compound of Formula (I) in combination with an additional pharmaceutical agent for the manufacture of a medicament for treating or preventing neurological and psychiatric disorders in which mGluR2 is involved.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a product comprising a compound of Formula (I) and an additional pharmaceutical agent, as a combined preparation for simultaneous, separate or sequential use in the treatment or prevention of neurological or psychiatric disorders and diseases.

The present invention relates in particular to compounds of Formula (I) as defined hereinabove, and the stereoisomeric forms thereof, wherein
R$^1$ is (C$_{3-8}$cycloalkyl)C$_{1-3}$alkyl, (C$_{1-3}$alkyloxy)C$_{1-3}$alkyl, and C$_{1-3}$alkyl;
and the pharmaceutically acceptable salts and the solvates thereof.

The present invention relates in particular to compounds of Formula (I) as defined hereinabove, and the stereoisomeric forms thereof, wherein
R$^1$ is (cyclopropyl)methyl or (ethyloxy)methyl;
and the pharmaceutically acceptable salts and the solvates thereof.

In a further embodiment, the present invention relates to compounds of Formula (I) as defined herein having the Formula (Ia)

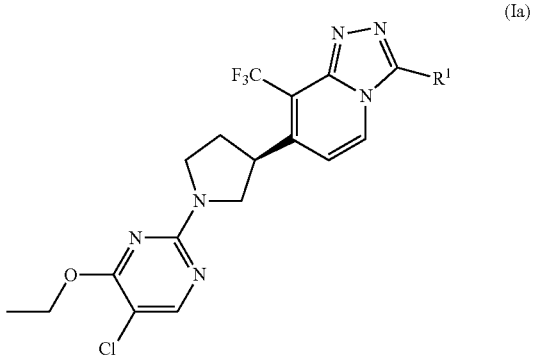

wherein R¹ is as defined in Formula (I) herein, and the pharmaceutically acceptable salts and the solvates thereof.

In a further embodiment, the present invention relates to compounds of Formula (I) as defined herein having the Formula (Ib)

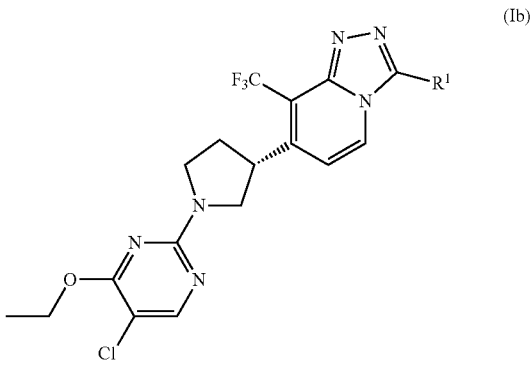

wherein R¹ is as defined in Formula (I) herein, and the pharmaceutically acceptable salts and the solvates thereof.

Particular compounds may be selected from the group of
7-[1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;
7-[(3*R)-1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;
7-[(3*S)-1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;
7-[1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine;
7-[(3*R)-1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine;
7-[(3*S)-1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine.

Included within the scope of this list are stereoisomeric forms, the pharmaceutically acceptable salts and the solvates thereof.

The names of the compounds of the present invention were generated according to the nomenclature rules agreed upon by the Chemical Abstracts Service (C.A.S.) using Advanced Chemical Development, Inc., software (ACD/Name product version 10.01.0.14105, October 2006). In case of tautomeric forms, the name of the depicted tautomeric form of the structure was generated. However it should be clear that the other non-depicted tautomeric form is also included within the scope of the present invention.

Definitions

The notation "$C_{1-3}$alkyl" or "$C_{1-6}$alkyl" as used herein alone or as part of another group, defines a saturated, straight or branched, hydrocarbon radical having, unless otherwise stated, from 1 to 3 or 1 to 6 carbon atoms, such as methyl, ethyl, 1-propyl, 1-methylethyl, butyl, 1-methyl-propyl, 2-methyl-1-propyl, 1,1-dimethylethyl, 3-methyl-1-butyl, 1-pentyl, 1-hexyl and the like.

The notation "$C_{3-8}$cycloalkyl" as used herein alone or as part of another group, defines a saturated, cyclic hydrocarbon radical having from 3 to 8 carbon atoms, such as cyclopropyl, cyclobutyl, cyclopentyl, cyclohexyl, cycloheptyl and cyclooctyl.

The notation "halogen" or "halo" as used herein alone or as part of another group, refers to fluoro, chloro, bromo or iodo, with fluoro or chloro being preferred.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible. The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above formula are intended to be included within the scope of the present invention.

It follows that a single compound may exist in both stereisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography or supercritical fluid chromatography (SFC) using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

Experimental Procedure 1

Final compounds according to Formula (I), can be prepared by reacting an intermediate of Formula (II) with 2,5-dichloro-4-ethoxy-pyrimidine in the presence of cesium fluoride, a base such as DIPEA and in an appropriate solvent solvent such as for example DMSO for a suitable period of time that allows the completion of the reaction, such as for example 2 h at a temperature between 80 and 100° C., such as 90° C. In reaction scheme 1, $R^1$ is as defined in Formula (I).

Reaction Scheme 1

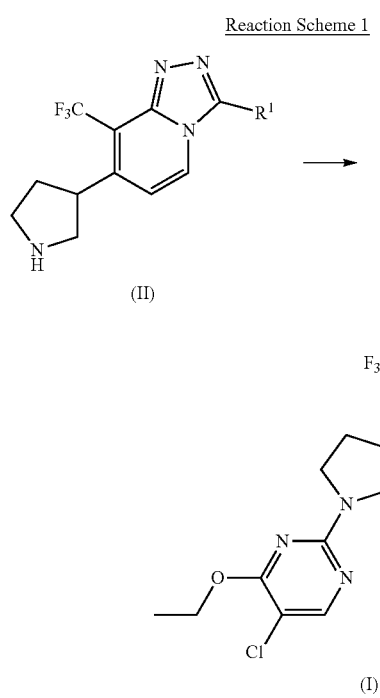

B. Preparation of the Intermediates
Experimental Procedure 2

Intermediate compounds according to Formula (II) can be prepared by cleaving the benzyl protecting group in the pyrrolidine ring in the intermediate compound of Formula (III), according to conditions known to the skilled person, such as for example subjecting an intermediate of Formula (III) to a reaction with 1-chloroethyl chloroformate in the presence of DIPEA in DCM for a suitable period of time that allows the completion of the reaction, such as a few minutes at rt. In reaction scheme 2, $R^1$ is defined as in Formula (I).

Reaction Scheme 2

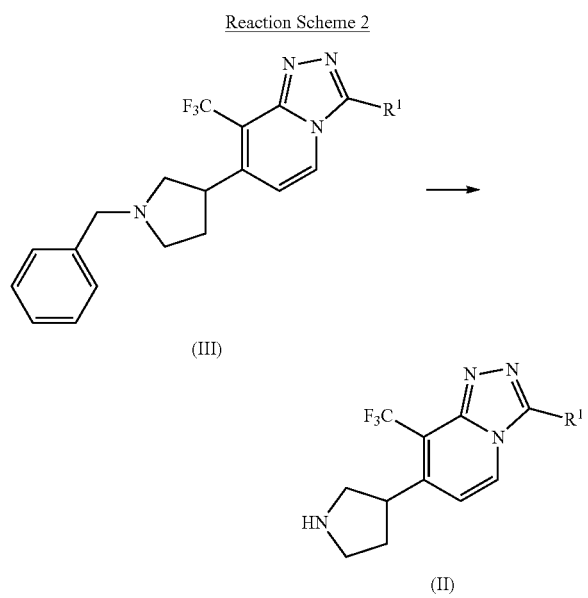

Experimental Procedure 3

Intermediate compounds according to Formula (III) can be prepared by reacting an intermediate of Formula (IV) with N-methoxymethyl-N-(trimethylsilylmethyl)benzylamine in the presence of an acid such as TFA, and in a suitable solvent, such as DCM for a period of time that allows the completion of the reaction, such as 1 h at rt. In reaction scheme 2, $R^1$ is as defined in Formula (I).

Reaction Scheme 3

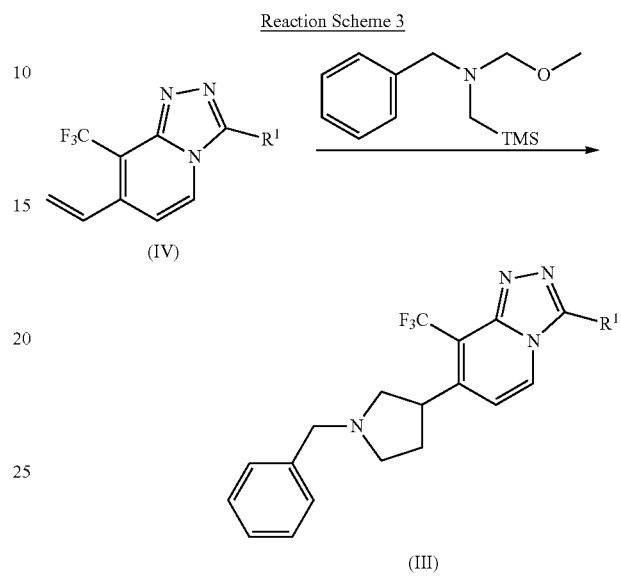

Experimental Procedure 4

Intermediate compounds according to Formula (IV) can be prepared by coupling reactions, such as Stille or Suzuki reactions of an intermediate of Formula (V) with a compound of Formula (VI) under conditions that are known to those skilled in the art. The process may be carried out optionally in a solvent such as 1,4-dioxane, water and generally at temperatures between about r.t and about 200° C. in the presence of a base. This is illustrated in reaction scheme (4) wherein all variables are defined as mentioned hereabove, wherein M is trialkyltin, boronic acid or boronate ester, and a palladium catalyst and halo is chloro, bromo or iodo.

Reaction Scheme 4

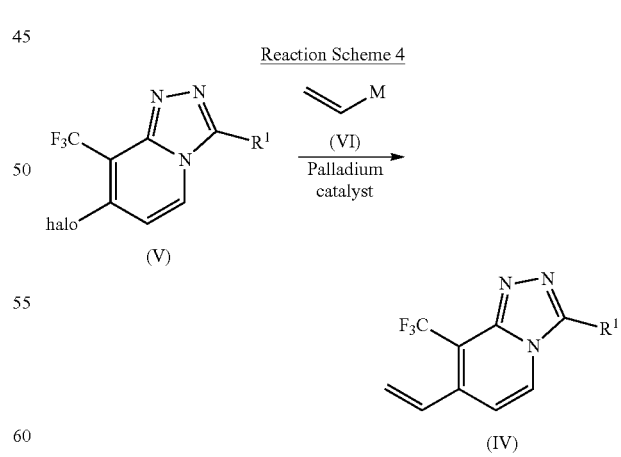

Experimental Procedure 5

Intermediate compounds according to Formula (V) can be prepared following art known procedures by cyclization of an intermediate compound of Formula (VII) in the presence of a halogenating agent such as for example phosphorus (V) oxychloride (POCl$_3$) in a suitable solvent such as, for example, dichloroethane, stirred under microwave irradiation, for a suitable period of time that allows the completion of the reaction, as for example 5 min at a temperature between 140-200° C. In reaction scheme (5), $R^1$ is defined as in Formula (I) and halo is chloro, bromo or iodo.

Reaction Scheme 5

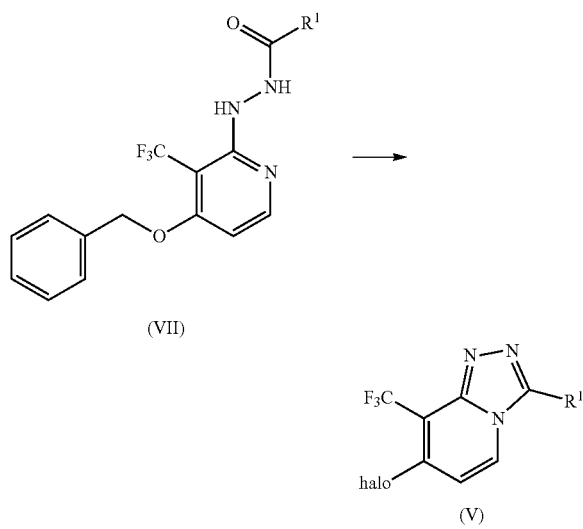

(VII)

(V)

Experimental Procedure 6

Intermediate compounds according to Formula (VII) can be prepared by art known procedures by reaction of a hydrazine intermediate of Formula (VIII) with acid halides of Formula (IX). The reaction can be carried out using an inert-solvent, such as for example DCM, in the presence of a base such as for example triethylamine, for example at r.t. for a suitable period of time that allows completion of the reaction, for example 20 min. In reaction scheme (6), $R^1$ is defined as in Formula (I).

Reaction Scheme 6

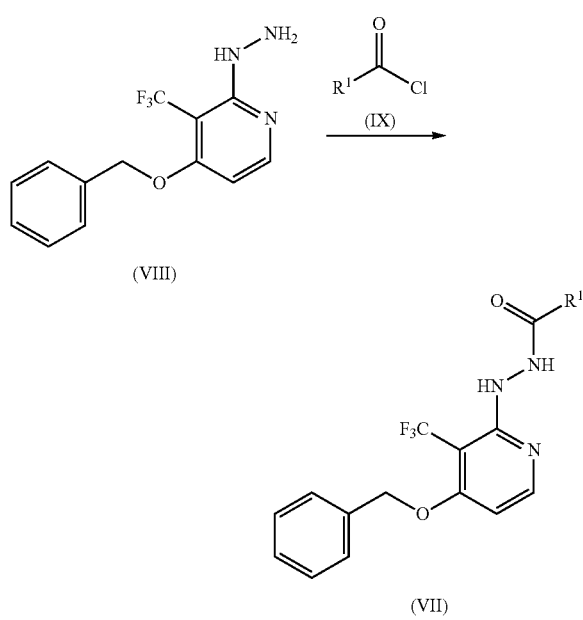

(VIII)

(VII)

Experimental Procedure 7

Intermediate compounds according to Formula (VIII) can be prepared by reacting an intermediate compound of Formula (X) with hydrazine according to reaction scheme (7), a reaction that is performed in a suitable reaction-inert solvent, such as, for example, ethanol, THF or 1,4-dioxane under thermal conditions such as, for example, heating the reaction mixture for example at 160° C. under microwave irradiation for 30 min or classical thermal heating at 70° C. for 16 h. In reaction scheme (7), halo is chloro, bromo or iodo.

Reaction Scheme 7

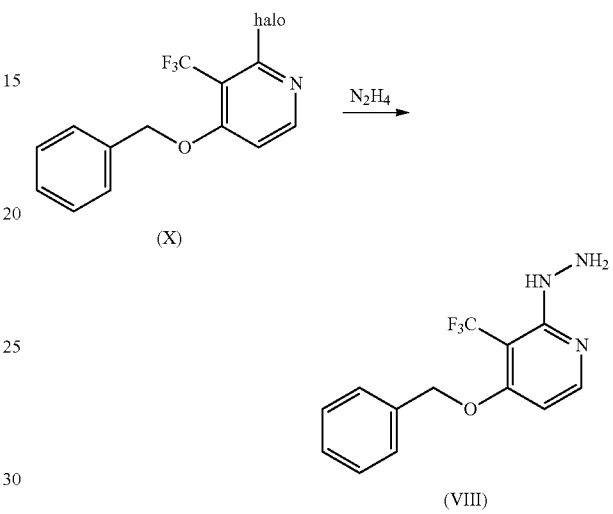

(X)

(VIII)

Experimental Procedure 8

Intermediate compounds according to Formula (X) can be prepared by reacting an intermediate compound of Formula (XI) with benzyl alcohol according to reaction scheme (8), a reaction that is performed in a suitable reaction-inert solvent, such as, for example, DMF in the presence of a suitable base, such as for example sodium hydride at r.t. for a suitable period of time that allows the completion of the reaction, such as for example 1 h. In reaction scheme (8), halo is chloro, bromo or iodo.

Reaction Scheme 8

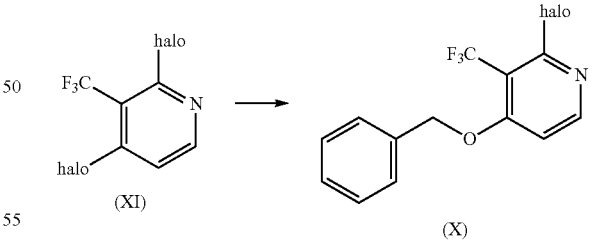

(XI)

(X)

Experimental Procedure 9

Intermediate compounds of Formula (XI), can be prepared by reacting an intermediate of Formula (XII), with a suitable trifluoromethylating agent, such as for example fluorosulfonyl(difluoro)acetic acid methyl ester, according to reaction scheme (9). This reaction is performed in a suitable reaction-inert solvent such as, for example, DMF in the presence of a suitable coupling agent such as for example, copper(I) iodide, under thermal conditions such as, for example, heating the reaction mixture for example at 160° C. under microwave irradiation for 45 min. In reaction scheme (9), halo is chloro, bromo or iodo.

Reaction Scheme 9

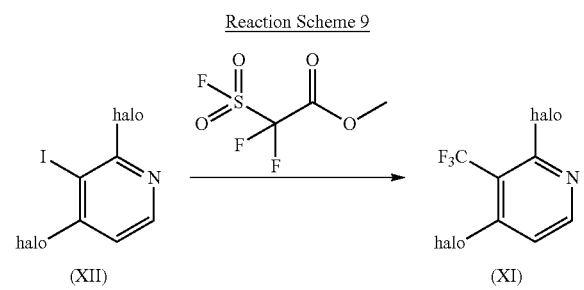

Experimental Procedure 10

Intermediate compounds of Formula (XII) can be prepared by reacting an intermediate compound of Formula (XIII) with a strong base, such as, for example, n-butyllithium, and further treatment with an iodinating agent such as, for example, iodine. This reaction is performed in suitable reaction-inert solvent such as, for example, THF at low temperature such as, for example −78° C. for a period of time that allows the completion of the reaction such as, for example 2 h. In reaction scheme (10), halo may be chloro, bromo or iodo.

Reaction Scheme 10

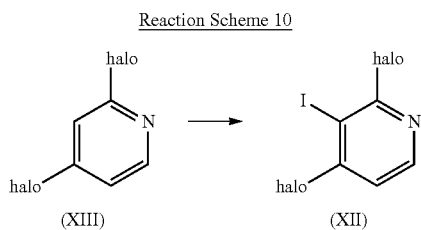

Starting material according to Formula (XIII) is either commercially available or may be prepared according to conventional reaction procedures generally known to those skilled in the art.

Pharmacology

The compounds provided in this invention are positive allosteric modulators (PAMs) of metabotropic glutamate receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), the stereoisomeric forms and the tautomers thereof and the pharmaceutically acceptable acid or base addition salts and the solvates thereof, for use as a medicament.

The invention also relates to the use of a compound according to the general Formula (I), the stereoisomeric forms and the tautomers thereof and the pharmaceutically acceptable acid or base addition salts and the solvates thereof, or a pharmaceutical composition according to the invention for the manufacture of a medicament.

The invention also relates to a compound according to the general Formula (I), the stereoisomeric forms and the tautomers thereof and the pharmaceutically acceptable acid or base addition salts and the solvates thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular positive allosteric modulators thereof.

The present invention also relates to the use of a compound according to the general Formula (I), the stereoisomeric forms and the tautomers thereof and the pharmaceutically acceptable acid or base addition salts and the solvates thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular positive allosteric modulators thereof.

The present invention also relates to a compound according to the general Formula (I), the stereoisomeric forms and the tautomers thereof and the pharmaceutically acceptable acid or base addition salts and the solvates thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of positive allosteric modulators of mGluR2.

Also, the present invention relates to the use of a compound according to the general Formula (I), the stereoisomeric forms and the tautomers thereof and the pharmaceutically acceptable acid or base addition salts and the solvates thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR2.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance dependence/abuse, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, major depressive disorder, treatment resistant depression, mania, bipolar disorders, such as bipolar mania), posttraumatic stress disorder, trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, autistic disorders, neurotoxicity and ischemia.

In particular, the central nervous system disorder is an anxiety disorder, selected from the group of agoraphobia, generalized anxiety disorder (GAD), mixed anxiety and depression, obsessive-compulsive disorder (OCD), panic disorder, posttraumatic stress disorder (PTSD), social phobia and other phobias. An additional anxiety disorder is panic attack.

In particular, the central nervous system disorder is a psychotic disorder selected from the group of schizophrenia, delusional disorder, schizoaffective disorder, schizophreniform disorder and substance-induced psychotic disorder; more in particular, negative symptoms or residual symptoms of schizophrenia. Such disorders manifest psychosis as a prominent symptom. Therefore, the invention also relates to a compound according to the general Formula (I), the stereoisomeric forms and the tautomers thereof and the pharmaceutically acceptable acid or base addition salts and the solvates thereof, or a pharmaceutical composition according to the invention for use in the treatment, prevention, amelioration, control or reduction of psychosis.

In particular, the central nervous system disorder is a personality disorder selected from the group of obsessive-compulsive personality disorder, borderline personality disorder and schizoid, schizotypal disorder.

In particular, the central nervous system disorder is a substance abuse or substance-related disorder selected from the group of alcohol abuse, alcohol addiction, alcohol dependence, alcohol withdrawal, alcohol withdrawal delirium, alcohol-induced psychotic disorder, amphetamine addiction, amphetamine dependence, amphetamine withdrawal, cocaine addiction, cocaine dependence, cocaine withdrawal, nicotine addiction, nicotine dependence, nicotine withdrawal, opioid dependence and opioid withdrawal. The treatment or prevention of the substance abuse or substance-related disorders referred to herein may involve relapse prevention thereof.

In particular, the central nervous system disorder is an eating disorder selected from the group of anorexia nervosa and bulimia nervosa.

In particular, the central nervous system disorder is a mood disorder selected from the group of bipolar disorders (I & II), cyclothymic disorder, depression, dysthymic disorder, major depressive disorder, treatment resistant depression, bipolar depression, and substance-induced mood disorder.

In particular, the central nervous system disorder is migraine.

In particular, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy. Additional disorders encompassed under epilepsy or convulsive disorder include any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), partial-onset seizures with or without generalization, myoclonic seizures, primary generalized tonic-clonic seizures in particular in patients with idiopathic generalized epilepsy, seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), status epilepticus (convulsive or non convulsive), essential tremor, restless limb syndrome, and the like. Preferably, the disorder is selected from epilepsy (regardless of type, underlying cause or origin), essential tremor or restless limb syndrome. More preferably, the disorder is epilepsy (regardless of type, underlying cause or origin) or essential tremor. In particular, the disorder is epilepsy (regardless of type, underlying cause or origin). A more particular example of epilepsy is refractory epilepsy, also referred to as treatment or therapy resistant epilepsy. This term is often used when patients have failed three or more anti-epileptic drugs (AEDs). Refractory epilepsy also includes refractory partial epilepsy and refractory generalized epilepsy (including idiopathic or symptomatic).

In particular, the central nervous system disorder is attention-deficit/hyperactivity disorder.

In particular, the central nervous system disorder is an autistic disorder selected from autism and autism spectrum disorders, such as Asperger's syndrome.

In particular, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, behavioral and psychological symptoms of dementia, substance-induced persisting dementia and mild cognitive impairment.

Particular examples of behavioral and psychological symptoms of dementia (BPSD) include, but are not limited to, aggression, agitation and psychosis.

In particular, the central nervous system disorder is selected from the group of schizophrenia, behavioral and psychological symptoms of dementia, major depressive disorder, treatment resistant depression, bipolar depression, anxiety, depression, generalised anxiety disorder, post-traumatic stress disorder, bipolar mania, epilepsy, attention-deficit/hyperactivity disorder, substance abuse and mixed anxiety and depression.

In particular, the central nervous system disorder is selected from the group of schizophrenia, epilepsy, obsessive compulsive disorder, alcohol addiction, cocaine addiction, nicotine addiction, borderline personality disorder, bipolar disorder, behavioral and psychological symptoms of dementia, Asperger's syndrome, major depressive disorder, treatment resistant depression, anxiety, depression, generalised anxiety disorder, and mixed anxiety and depression.

In particular, the central nervous system disorder is selected from the group of schizophrenia (in particular, negative symptoms or residual symptoms thereof), generalized anxiety disorder, bipolar disorder (I or II), migraine, behavioral and psychological symptoms of dementia, epilepsy or convulsive disorders, panic disorder, mixed anxiety and depression, and agoraphobia.

In particular, the central nervous system disorder is selected from the group of schizophrenia (in particular, negative symptoms or residual symptoms thereof), generalized anxiety disorder, bipolar disorder (I or II), migraine, epilepsy, panic disorder, mixed anxiety and depression, and agoraphobia. Of the disorders mentioned above, the treatment of psychosis, schizophrenia, behavioral and psychological symptoms of dementia, major depressive disorder, treatment resistant depression, bipolar depression, anxiety, depression, generalised anxiety disorder, post-traumatic stress disorder, bipolar mania, substance abuse and mixed anxiety and depression, are of particular importance.

Of the disorders mentioned above, the treatment of generalized anxiety disorder, bipolar disorder (I or II), epilepsy, panic disorder, and agoraphobia are of particular importance.

Of the disorders mentioned above, the treatment of anxiety, schizophrenia, migraine, depression, and epilepsy are of particular importance.

Of the disorders mentioned above, the treatment of anxiety and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as anxiety disorders, in particular, agoraphobia, generalized anxiety disorder, panic disorder, social anxiety disorder (social phobia), and panic attack; schizophrenia spectrum and other psychotic disorders, in particular, schizophrenia, delusional disorder, schizoaffective disorder, schizophreniform disorder, substance/medication-induced and psychotic disorder; personality disorders, in particular, obsessive-compulsive personality disorder, borderline personality disorder, schizoid personality disorder, and schizotypal personality disorder; substance-related and addictive disorders, in particular, alcohol use disorder, alcohol withdrawal, opioid use disorder, opioid withdrawal, stimulant (amphetamine-type substance, cocaine) use disorder, stimulant (amphetamine-type substance, cocaine) withdrawal, tobacco use disorder, and tobacco withdrawal; depressive disorders, in particular, major depressive disorder, persistent depressive disorder (dysthymia), and substance/medication-induced depressive disorder; bipolar and related disorders, in particular, bipolar I disorder, bipolar II disorder, cyclothymic disorder, substance/medication-induced bipolar and related disorder; obsessive-compulsive disorder and related disorders, in particular, obsessive-compulsive disorder; trauma- and stressor-related disorders, in particular, posttraumatic stress disorder, and acute stress disorder; neurodevelopmental disorder, in particular, autism spectrum disorder, and attention-deficit/hyperactivity disorder; neurocognitive disorders (NCDs) (both major and mild), in particular, delirium, substance intoxication delirium, NCD due to Alzheimer's disease, NCD due to HIV infection, NCD due to Huntington's disease, NCD due to Parkinson's disease, and substance/medication-induced NCD. Such terms may be used by the skilled person as an alternative nomenclature for some of the diseases or conditions referred to herein.

Therefore, the invention also relates to a compound according to the general Formula (I), the stereoisomeric forms and the tautomers thereof and the pharmaceutically acceptable acid or base addition salts and the solvates thereof, for use in the treatment of any one of the diseases mentioned hereinbefore.

The invention also relates to a compound according to the general Formula (I), the stereoisomeric forms and the tautomers thereof and the pharmaceutically acceptable acid or base addition salts and the solvates thereof, for use in treating any one of the diseases mentioned hereinbefore.

The invention also relates to a compound according to the general Formula (I), the stereoisomeric forms and the tautomers thereof and the pharmaceutically acceptable acid or base addition salts and the solvates thereof, for the treatment or prevention, in particular treatment, of any one of the diseases mentioned hereinbefore.

The invention also relates to the use of a compound according to the general Formula (I), the stereoisomeric forms and the tautomers thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms and the tautomers thereof and the pharmaceutically acceptable acid or base addition salts and the solvates thereof, for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form or a tautomer thereof and a pharmaceutically acceptable addition salt or solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a patient in need thereof.

One skilled in the art will recognize that a therapeutically effective amount of the PAMs of the present invention is the amount sufficient to modulate the activity of the mGluR2 and that this amount varies inter alia, depending on the type of disease, the concentration of the compound in the therapeutic formulation, and the condition of the patient. Generally, an amount of PAM to be administered as a therapeutic agent for treating diseases in which modulation of the mGluR2 is beneficial, such as the disorders described herein, will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist (or mGluR2/3 agonist). Examples of mGluR2/mGluR2/3 agonists include, for example, LY-379268; DCG-IV; LY-354740; LY-404039; LY-544344; LY-2140023; LY-181837; LY-389795; LY-446433; LY-450477; talaglumetad; MGS0028; MGS0039; (−)-2-oxa-4-aminobicyclo[3.1.0]hexane-4,6-dicarboxylate; (+)-4-amino-2-sulfonylbicyclo[3.1.0]hexane-4,6-dicarboxylic acid; (+)-2-amino-4-fluorobicyclo-[3.1.0]hexane-2,6-dicarboxylic acid; 1S,2R,5S,6S-2-amino-6-fluoro-4-oxobicyclo-[3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R,3R,5S,6S-2-amino-3-fluorobicyclo[3.1.0]hexane-2,6-dicarboxylic acid; 1S,2R,3S,5S,6S-2-amino-6-fluoro-3-hydroxybicyclo[3.1.0]hexane-2,6-dicarboxylic acid; (+)-4-amino-2-sulfonylbicyclo-[3.1.0]hexane-4,6-dicarboxylic acid; (+)-2-amino-4-fluorobicyclo[3.1.0]hexane-2,6-dicarboxylic acid; 1S,2R,5S,6S-2-amino-6-fluoro-4-oxobicyclo[3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R,3R,5S,6S-2-amino-3-fluorobicyclo[3.1.0]hexane-2,6-dicarboxylic acid; or 1S,2R,3S,5S,6S-2-amino-6-fluoro-3-hydroxybicyclo-[3.1.0]hexane-2,6-dicarboxylic acid. More preferable mGluR2 agonists include LY-379268; DCG-IV; LY-354740; LY-404039; LY-544344; or LY-2140023.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The present invention also provides compositions for preventing or treating diseases in which modulation of the mGlu2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form or a tautomer thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms and the tautomers thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included.

Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an mGluR2 orthosteric agonist (or a mGluR2/3 orthosteric agonist). The present invention also relates to such a combination for use as a medicine. The present invention also relates to a product comprising (a) a compound according to the present invention, a pharmaceutically acceptable salt thereof or a solvate thereof, and (b) a mGluR2 orthosteric agonist (or a mGluR2/3 orthosteric agonist), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular positive mGluR2 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Herein, "aq." means aqueous; "BEH" bridged ethylsiloxane/silica hybrid; "CSH" charged surface hybrid; "DAD" Diode Array Detector; "DCM" means dichloromethane; "DIPEA" means N,N-diisopropylethylamine; "DMF" means N,N-dimethylformamide; "DMSO" means dimethyl sulfoxide; "Et$_2$O" means diethyl ether; "EtOAc" means ethyl acetate; "h" means hour(s); "HPLC" means high performance liquid chromatography; "iPr" means isopropyl; "l" or "L" means liter; "LCMS" means liquid chromatography mass spectrometry; "MeOH" means methanol; "min" means minute(s); "mp" means melting point; "MSD" Mass Selective Detector; "Pd(PPh$_3$)$_4$" means tetrakis(triphenylphosphine)palladium(0); "RP" means reverse phase; "r.t." or "R.T." mean room temperature; "s" means seconds; "sat." means saturated; "SFC" means supercritical fluid chromatography; "sol." means solution; "SQD" Single Quadrupole Detector; "TFA" means trifluoroacetic acid; "THF" means tetrahydrofuran; "UPLC" Ultra Performance Liquid Chromatography.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from Merck, on irregular silica gel, particle size 15-40 μm (normal phase disposable flash columns) on a SPOT or LAFLASH system from Armen Instrument.

The absolute stereochemical configuration for some of the compounds was determined using vibrational circular dichroism (VCD). They were measured on a Bruker Equinox 55 equipped with a PMA 37, in a KBr liquid cell using CD$_2$Cl$_2$ as solvent (PEM: 1350 cm-1, LIA: 1 mV, resolution: 4 cm$^{-1}$). A description on the use of VCD for the determination of absolute configuration can be found in Dyatkin A. B. et. al, Chirality, 14:215-219 (2002).

Whenever the notation "RS" is indicated herein, it denotes that the compound is a racemic mixture, unless otherwise indicated. The stereochemical configuration for some compounds has been designated "R" or "S" when the mixture was separated; for some compounds, the stereochemical configuration has been designated as "*R" or "*S" when the absolute stereochemistry is undetermined although the compound itself has been isolated as a single stereoisomer and is enantiomerically pure. The enantiomeric excess of compounds reported herein was determined by analysis of the racemic mixture by supercritical fluid chromatography (SFC) followed by SFC comparison of the separated enantiomer(s).

PREPARATION OF INTERMEDIATES

Intermediate 1 (I-1)

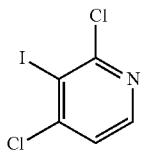

To a solution of 2,4-dichloropyridine (5.2 g, 35.137 mmol) and diisopropylamine (3.911 g, 38.651 mmol) in dry THF (40 ml) cooled at −78° C. under a nitrogen atmosphere, was added n-butyllithium (24.157 ml, 38.651 mmol, 1.6 M in hexanes) dropwise. The resulting reaction mixture was stirred at −78° C. for 45 min and then a solution of iodine (9.81 g, 38.651 mmol) in dry THF (20 ml) was added dropwise. The mixture was stirred at −78° C. for 1 h, allowed to warm to rt, diluted with EtOAc and quenched with NH$_4$C$_1$ (aqueous sat. solution) and Na$_2$S$_2$O$_3$ (aqueous sat. solution). The organic layer was separated, washed with NaHCO$_3$ (aqueous sat. solution), dried (Na$_2$SO$_4$) and concentrated in vacuo. The crude product was purified by column chromatography (silica gel; heptane/DCM up to 20% as eluent). The desired fractions were collected and concentrated in vacuo to yield I-1 (7.8 g, 81%).

Intermediate 2 (I-2)

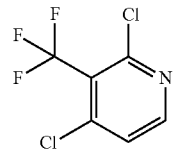

To a mixture of I-1 (2 g, 7.302 mmol) in DMF (50 mL) were added fluorosulfonyl-difluoro-acetic acid methyl ester ([CAS 680-15-9], 1.858 mL, 14.605 mmol) and copper (I) iodide (2.796. g, 14.605 mmol). The reaction mixture was heated in a sealed tube at 100° C. for 5 h. After cooling, the solvent was evaporated in vacuo. The crude product was purified by column chromatography (silica gel; DCM as eluent). The desired fractions were collected and concentrated in vacuo to yield I-2 (1.5 g, 95%).

Intermediate 3 (I-3)

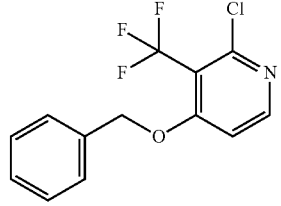 [SMILES: FC(F)(F)c1c(OCc2ccccc2)ccnc1Cl]

To a suspension of NaH (0.487 g, 12.732 mmol, 60% mineral oil) in DMF (50 mL) cooled at 0° C., was added benzyl alcohol (1.262 mL, 12.2 mmol). The resulting mixture was stirred for 2 min, then, I-2 (2.5 g, 11.575 mmol) was added. The resulting reaction mixture was gradually warmed to rt and stirred for 1 h. The reaction mixture was quenched with water and extracted with Et$_2$O. The organic layer was separated, dried (Na$_2$SO$_4$) and concentrated in vacuo. The crude product was purified by column chromatography (silica gel; Heptane/DCM gradient as eluent). The desired fractions were collected and concentrated in vacuo to yield I-3 (1.1 g, 33%).

Intermediate 4 (I-4)

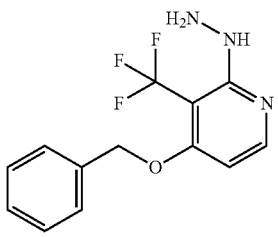 [SMILES: NNc1nccc(OCc2ccccc2)c1C(F)(F)F]

To a suspension of I-3 (1.09 g, 3.789 mmol) in 1,4-dioxane (9 mL), was added hydrazine monohydrate (3.676 mL, 75.78 mmol). The reaction mixture was heated at 160° C. under microwave irradiation for 30 min. After cooling, the resulting solution was concentrated in vacuo. The residue thus obtained was dissolved in DCM and washed with NaHCO$_3$ (aqueous sat. solution). The organic layer was separated, dried (Na$_2$SO$_4$) and concentrated in vacuo to yield I-4 (0.890 g, 83%) as a white solid.

Intermediate 5 (I-5)

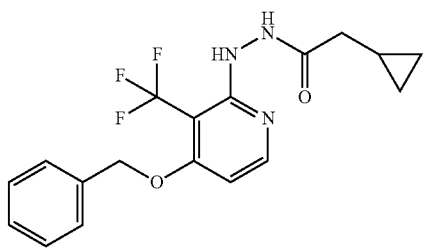 [SMILES: O=C(CC1CC1)NNc1nccc(OCc2ccccc2)c1C(F)(F)F]

To a solution of I-4 (0.890 g, 3.142 mmol) in dry DCM (3 mL) was added Et$_3$N (0.653 mL, 4.713 mmol) and cyclopropyl-acetyl chloride ([CAS 543222-65-5], 0.373 g, 3.142 mmol). The resulting reaction mixture was stirred at 0° C. for 20 min. The resulting mixture was then concentrated in vacuo to yield I-5 (1.1 g, 96%).

Intermediate 6 (I-6)

In a manner analogous to the synthesis of I-5, the following intermediate was also synthesized:

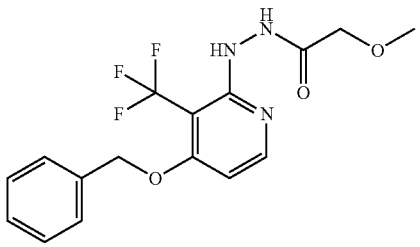

Addition performed at 0° C., mixture stirred at rt for 16 h; starting material: I-4 (8 g), reagent: 2-methoxy-acetyl chloride (3.807 g), yielded I-6 (11.219 g, 97%) as an oil that precipitated upon standing.

Intermediate 7 (I-7)

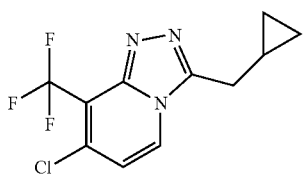 [SMILES: FC(F)(F)c1c(Cl)ccn2c(CC3CC3)nnc12]

I-5 (1.14 g, 1.872 mmol) and phosphorous (V) oxychloride (0.349 g, 3.744 mmol) in CH$_3$CN (10 mL) were heated at 150° C. under microwave irradiation for 10 min. After cooling, the resulting reaction mixture was diluted with DCM and washed with NaHCO$_3$ (aqueous sat. solution), dried (Na$_2$SO$_4$) and concentrated in vacuo. The crude product was purified by column chromatography (silica gel; DCM/7M solution of NH$_3$ in MeOH up to 20% as eluent). The desired fractions were collected and concentrated in vacuo to yield I-7 (0.261 g, 51%) as a white solid.

Intermediate 8 (I-8)

In a manner analogous to the synthesis of I-7, the following intermediate was also synthesized:

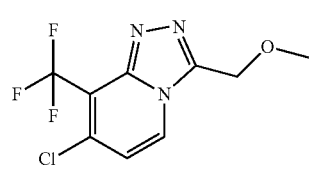

Reaction performed in 3 batches; starting material: I-6 (4.7 g), yielded I-8 (2.11 g, 59%) as a white solid.

Intermediate 9 (I-9)

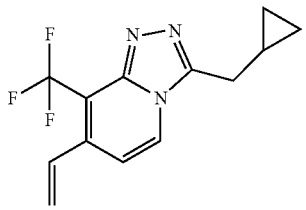 [SMILES: C=Cc1ccn2c(CC3CC3)nnc2c1C(F)(F)F]

A suspension of I-7 (1.65 g, 5.986 mmol), vinylboronic acid pinacol ester (1.218 mL, 7.183 mmol), Pd(PPh$_3$)$_4$ (0.346, 0.3 mmol) and NaHCO$_3$ (aqueous sat. solution, 12.5 mL) in 1,4-dioxane (64.5 mL) was heated at 150° C. under microwave irradiation for 13 min. After cooling, the resulting reaction mixture was diluted with EtOAc/water and filtered through a pad of diatomaceous earth. The filtrate was washed with water and NaCl (aqueous sat. solution) and extracted with EtOAc. The organic layer was separated, dried (Na$_2$SO$_4$) and concentrated in vacuo. The residue was purified again by column chromatography (silica gel; DCM/EtOAc from 100/0 to 60/40 as eluent). The desired fractions were collected and concentrated in vacuo to yield I-9 (1.34 g, 83.7%).

Intermediate 10 (I-10)

In a manner analogous to the synthesis of I-9, the following intermediate was also synthesized:

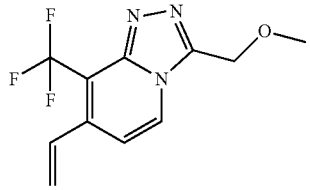

I-10

Starting material: I-8 (4.91 g), yielded I-10 (3.65 g, 79%) as a white solid.

Intermediate 11 (I-11)

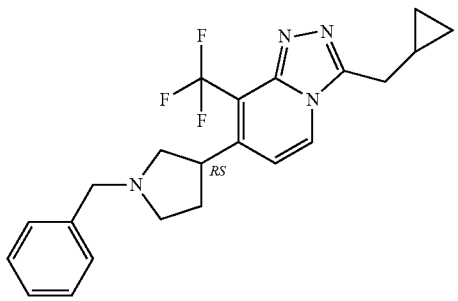 [SMILES: FC(F)(F)c1c(C2CCN(Cc3ccccc3)C2)ccn2c(CC3CC3)nnc12]

TFA (57.269 μL, 0.748 mmol) was added to a solution of I-9 (2000 mg, 7.484 mmol) in DCM (150 mL) at rt, then N-methoxymethyl-N-(trimethylsilylmethyl)benzylamine ([CAS 93102-05-7], 5.744 mL, 22.451 mmol) was added dropwise and the resulting solution was stirred for 3 h. Then the reaction mixture was washed with aqueous solution of NaHCO$_3$ (10%). The organic layer was separated, dried (Na$_2$SO$_4$), filtered and concentrated in vacuo. The residue was purified by flash column chromatography (silica; MeOH in DCM 0/100 to 3/97). The desired fractions were collected and concentrated in vacuo to give a pale yellow oil which was triturated with diisopropylether to give I-11 (1.42 g, 47%) as a white solid. LCMS: R$_t$ 2.29 min, m/z 401 [M+H]$^+$, 459 [M+CH$_3$COO]$^-$(method 1). $^1$H NMR (400 MHz, DMSO-d$_6$) δ ppm 0.27-0.41 (m, 2 H) 0.49-0.63 (m, 2 H) 1.17-1.33 (m, 1 H) 1.76-1.89 (m, 1 H) 2.31-2.43 (m, 1 H) 2.48 (q, J=8.1 Hz, 1 H) 2.68-2.77 (m, 1 H) 2.81 (dd, J=9.9, 3.9 Hz, 1 H) 3.01 (td, J=8.3, 2.8 Hz, 1 H) 3.10 (d, J=6.9 Hz, 2 H) 3.64-3.79 (m, 2 H) 3.79-3.91 (m, 1 H) 7.28-7.34 (m, 1 H) 7.35-7.46 (m, 5 H) 8.75 (d, J=7.4 Hz, 1 H).

Intermediate 12 (I-12)

In a manner analogous to the synthesis of I-11, the following intermediate was also synthesized:

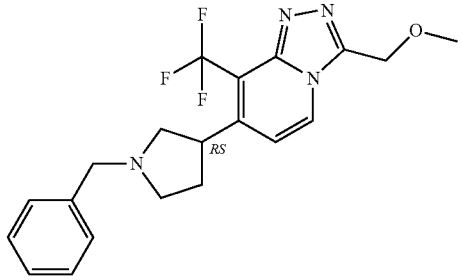

I-12

Starting material: I-10 (2.87 g), yielded I-12 (1.5 g, 35%) as a white solid. LCMS: Rt 2.28 min, m/z 405 [M+H]$^+$, 463 [M+CH$_3$COO]$^-$(method 1). $^1$HNMR (400 MHz, CDCl$_3$) δ ppm 1.21 (t, J=6.9 Hz, 3 H) 1.74-1.89 (m, 1 H) 2.35-2.50 (m, 2 H) 2.68 (dd, J=9.7 Hz, 1 H) 2.86 (dd, J=10.2, 2.8 Hz, 1 H) 3.02-3.15 (m, 1 H) 3.55 (q, J=6.9 Hz, 2 H) 3.63 (d, J=12.9 Hz, 1 H) 3.75 (d, J=12.7 Hz, 1 H) 3.86-4.02 (m, 1 H) 5.05 (s, 2 H) 7.24-7.30 (m, 1 H) 7.31-7.40 (m, 4 H) 7.46 (d, J=7.4 Hz, 1 H) 8.33 (d, J=7.4 Hz, 1 H).

Intermediate 13 (I-13)

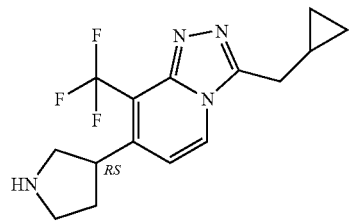 [SMILES: FC(F)(F)c1c(C2CCNC2)ccn2c(CC3CC3)nnc12]

1-Chloro ethyl chloroformate ([CAS 50893-53-3], 168.407 μL, 1.561 mmol) was added to a stirred solution of I-11 (250 mg, 0.624 mmol) and DIPEA (376.546 μL, 2.185 mmol) in DCM (5 mL) and the mixture was stirred at RT for 4 h. Then a saturated solution of NaHCO$_3$ was added and the mixture was stirred at RT for 5 min. The organic layer was separated, dried (MgSO$_4$), filtered, and the solvent was evaporated in vacuo. The residue was dissolved in MeOH (5 mL) and the mixture was stirred at RT for 16 h. Then the solvent was evaporated and the residue was purified by flash column chromatography (silica gel, 7N NH$_3$ in MeOH in DCM, 0/100 to 4/96). The desired fractions were collected and evaporated in vacuo to yield I-13 (155 mg, 80%) as brownish solid. LCMS: R$_t$ 0.62 min, m/z 311 [M+H]$^+$ (method 2). $^1$H NMR (400 MHz, CDCl$_3$) δ ppm 0.26-0.42 (m, 2 H) 0.55-0.70 (m, 2 H) 1.10-1.24 (m, 1 H) 1.82 (dq, J=13.4, 7.6 Hz, 1 H) 2.27-2.41 (m, 1 H) 2.95 (dd, J=11.1, 6.2 Hz, 1 H) 3.09 (d, J=6.7 Hz, 2 H) 3.13 (dt, J=10.6, 7.4 Hz, 1 H) 3.23 (dq, J=10.6, 4.2 Hz, 1 H) 3.39 (dd, J=11.1, 8.1 Hz, 1 H) 3.83 (br. quin, J=7.6, 7.6, 7.6, 7.6, 1 H) 7.06 (d, J=7.4 Hz, 1 H) 8.06 (d, J=7.4 Hz, 1 H).

Intermediate 14 (I-14)

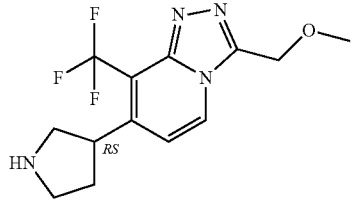 [SMILES: COCc1nnc2c(C(F)(F)F)c(C3CCNC3)ccn12]

1-Chloro ethyl chloroformate ([CAS 50893-53-3], 1.014 mL, 9.396 mmol) was added to a stirred solution of I-12 (1.52 g, 3.758 mmol) and DIPEA (2.267 mL, 13.154 mmol) in MeOH (30.1 mL, 743.06 mmol) at 0° C. and the mixture was stirred at RT for 4 h. Then a saturated solution of NaHCO$_3$ was added and the mixture was stirred at RT for 5 min. The organic layer was separated, dried (MgSO$_4$), filtered, and the solvent was evaporated in vacuo. The residue was dissolved in MeOH and the mixture was stirred at RT for 48 h. Then the solvent was evaporated and the residue was purified by flash column chromatography (silica gel, 7N NH$_3$ in MeOH in CH$_2$Cl$_2$, 0/100 to 50/50. The desired fractions were collected and evaporated in vacuo to yield I-14 (700 mg, 59%) as a brownish solid. LCMS: R$_t$ 0.36 min, m/z 315 [M+H]$^+$(method 3). $^1$H NMR (400 MHz, CDCl$_3$) δ ppm 1.21 (t, J=6.9 Hz, 3 H) 1.79-1.92 (m, 1 H) 2.28-2.43 (m, 1 H) 2.99 (dd, J=11.1, 6.2 Hz, 1 H) 3.15 (dt, J=10.4, 7.4 Hz, 1 H) 3.27 (dq, J=10.6, 4.2 Hz, 1 H) 3.42 (dd, J=11.1, 8.3 Hz, 1 H) 3.56 (q, J=6.9 Hz, 2 H) 3.85 (br. quin, J=8.1, 8.1, 8.1, 8.1 Hz, 1 H) 5.06 (s, 2 H) 7.12 (d, J=7.4 Hz, 1 H) 8.35 (d, J=7.4 Hz, 1 H).

Synthesis of Final Compounds

Example 1

Synthesis of Compounds 1, 1a and 1b (Co. No. 1, Co. No. 1a and Co. No. 1b)

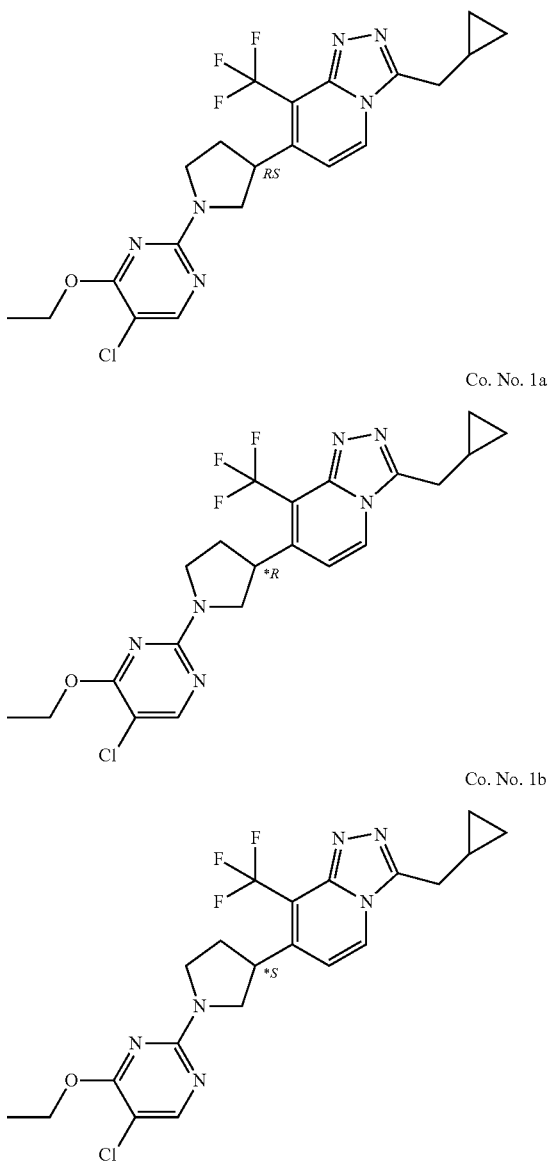

A mixture of 2,5-dichloro-4-ethoxy-pyrimidine ([CAS 1351762-11-2], 376.88 mg, 1.952 mmol), I-13 (792 mg, 2.169 mmol—obtained from the combination of two batches) and cesium fluoride (988.599 mg, 6.508 mmol), DIPEA (373.84 μL, 2.169 mmol) in DMSO (15 mL) was heated at 90° C. for 2 h. Then the mixture was diluted with a staturated solution of NaCl and extracted with EtOAc (×3). The combined organic layers were extracted with a saturated solution of NaCl, dried over MgSO$_4$, filtered and concentrated in vacuo. The crude was purified by flash column chromatography (silica; 7N NH$_3$ in MeOH in DCM 0/100 to 2/98). The desired fractions were collected and concentrated in vacuo. The residue thus obtained was purified by RP HPLC (Stationary phase: C18 XBridge 30×100 mm 5 μm; mobile phase: Gradient from 60% 0.1% NH$_4$CO$_3$H/NH$_4$OH pH 9 solution in water, 40% CH$_3$CN to 43% 0.1% NH$_4$CO$_3$H/NH$_4$OH pH 9 solution in water, 57% CH$_3$CN). The desired fractions were collected and evaporated in vacuo to yield Co. No. 1 (652 mg, 64%) as pale yellow foam.

A purification was performed via chiral SFC (Stationary phase: Chiralpak AD-H 5 μm 250*30 mm, Mobile phase: 60% CO$_2$, 40% iPrOH) to yield Co. No. 1a (262 mg, 26%) and Co. No. 1b (243 mg, 24%).

Example 2

In a manner analogous to the synthesis of compounds 1, 1a and 1b, the following compounds were also synthesized:

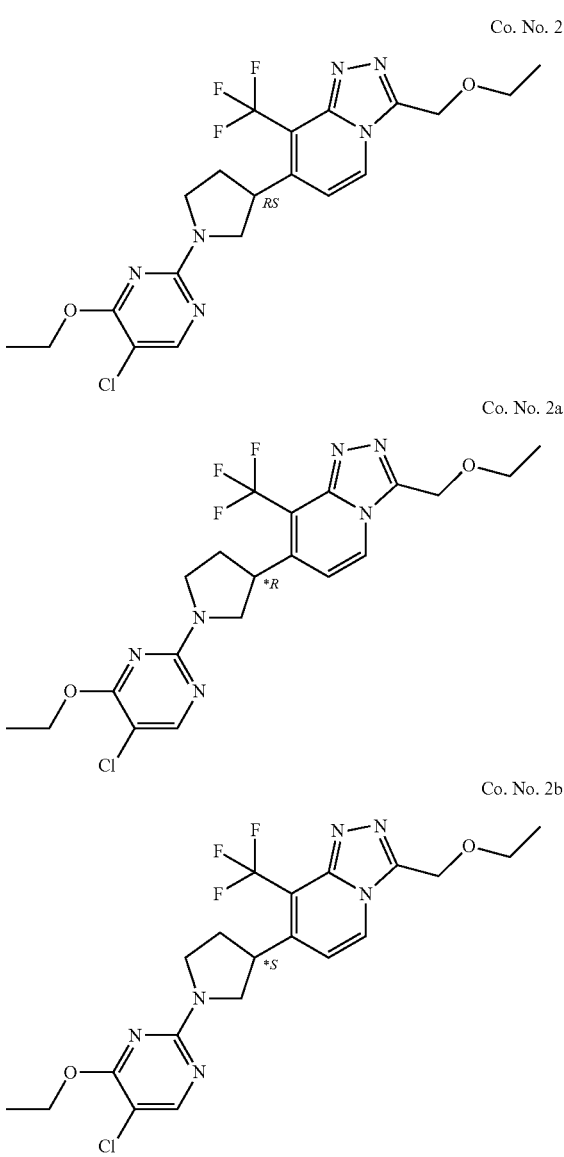

Starting material: I-14 (700 mg)

Chiral SFC conditions on Co. No. 2 (500 mg after trituration with diisopropyl ether): Stationary phase: Chiralpak AD-H 5 μm 250*30 mm, Mobile phase: 75% CO$_2$, 25% iPrOH (0.3% iPrNH$_2$) yielding 227 mg (22%) Co. No. 2a and 223 mg (22%) Co. No. 2b.

Table 1 below the compounds of Formula (I) which were prepared by analogy to the above examples (Exp. no.).

TABLE 1

Example compounds according to Formula (I).
# indicates that the experimental procedure is described in the examples.

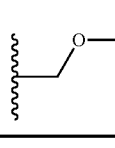

| Co. No. | Exp no. | R¹ | Stereo-chem. |
|---|---|---|---|
| 1 | 1* | (cyclopropylmethyl) | RS |
| 1a | 1* | (cyclopropylmethyl) | *R |
| 1b | 1* | (cyclopropylmethyl) | *S |
| 2 | 2* | (ethoxymethyl) | RS |
| 2a | 2* | (ethoxymethyl) | *R |
| 2b | 2* | (ethoxymethyl) | *S |

Analytical Part

Melting Points

Values are peak values, and are obtained with experimental uncertainties that are commonly associated with this analytical method.

DSC823e (A): For a number of compounds, melting points (m.p.) were determined with a DSC823e (Mettler-Toledo) apparatus. Melting points were measured with a temperature gradient of 10° C./minute. Maximum temperature was 300° C. Peak values were recorded.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, $[M+CH_3COO]^-$ etc. . . . ). For molecules with multiple isotopic patterns (Br, Cl . . . ), the reported value is the one obtained for the lowest isotope mass. All results were obtained with experimental uncertainties that are commonly associated with the method used.

TABLE 2

LC-MS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| 1 | Waters: Acquity® UPLC® - DAD/SQD | Waters: CSH™ C18 (1.7 μm, 2.1 × 50 mm) | A: 95% CH₃COONH₄ 6.5 mM + 5% CH₃CN, B: CH₃CN | From 95% A to 5% A in 4.6 min, held for 0.4 min | 1 50 | 5 |

TABLE 2-continued

LC-MS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| 2 | Agilent: HP1100-DAD, Waters: SQD | Agilent: Eclipse Plus C18 (3.5 μm, 2.1 × 30 mm) | A: 95% $CH_3COONH_4$ 6.5 mM + 5% $CH_3CN$, B: 1/1 $CH_3CN$/$CH_3OH$, | 95% A kept for 0.2 min, to 0% A in 2.8 min, held for 0.15 min, back to 95% A in 0.15 min, held for 1.7 min | 1 60 | 5 |
| 3 | Agilent: HP1100-DAD, Waters: SQD | Agilent: Eclipse Plus C18 (3.5 μm, 2.1 × 30 mm) | A: 95% $CH_3COONH_4$ 6.5 mM + 5% $CH_3CN$, B: 1/1 $CH_3CN$/$CH_3OH$, | 95% A kept for 0.2 min, to 0% A in 0.8 min, held for 0.15 min, back to 95% A in 0.15 min, held for 1.7 min | 1 60 | 3 |
| 4 | Waters: Acquity UPLC ® - DAD/ Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |

TABLE 3

Physico-chemical data for some compounds, retention time ($R_t$) in min, $[M + H]^+$ peak (protonated molecule), LCMS method and mp (melting point in ° C.).

| Co. No. | mp (° C.) | $R_t$ | $[M + H]^+$ | Adduct | Method |
|---|---|---|---|---|---|
| 1 | n.d. | 3.13 | 467 |  | 2 |
| 1a | 167.64 | 2.57 | 467 | 525 $[M + CH_3COO]^-$ | 1 |
| 1b | 168.29 | 2.57 | 467 | 525 $[M + CH_3COO]^-$ | 1 |
| 2 | 153.86 | 2.52 | 471 | 469 | 1 |
| 2a | n.d. | 3.13 | 471 | 529.1 $[M + CH_3COO]^-$ | 4 |
| 2b | n.d. | 3.13 | 471 | 529.1 $[M + CH_3COO]^-$ | 4 |

(n.d. = not determined).

SFC/MS

General Procedure

The SFC measurement was performed using Analytical Supercritical fluid chromatography (SFC) system composed by a binary pump for delivering carbon dioxide (CO2) and modifier, an autosampler, a columns oven with switching valve for column heating from room temperature to 80° C., a diode array detector equipped with a high-pressure flow cell standing up to 400 bars. Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software

TABLE 4

Analytical SFC-MS Methods (Flow expressed in mL/min; column temperature (T) in ° C.; Pressure in MPa).

| Method | Column | Mobile Phase | Flow | T | Pressure |
|---|---|---|---|---|---|
| 1 | Chiralpak AD 150 × 4.6 mm, 5 μm Daicel | $CO_2$/EtOH (0.3% $IPrNH_2$) 70/30 | 3 | 35 | 100 |
| 2 | Chiralpak AD 150 × 4.6 mm, 5 μm Daicel | $CO_2$/EtOH (0.3% $IPrNH_2$) 80/20 | 3 | 35 | 100 |

TABLE 5

Analytical SFC data - $R_t$ means retention time (in minutes), $[M + H]^+$ means the protonated mass of the compound, method refers to the method used for SFC/MS analysis of enantiomerically pure compounds. The measurement was compared against the mixture.

| Co. Nr. | $R_t$ | $[M + H]^+$ | UV Area % | Method | Isomer Elution Order* |
|---|---|---|---|---|---|
| 1a | 3.03 | 467 | 100 | 1 | A |
| 1b | 3.59 | 467 | 98.99 | 1 | B |
| 2a | 4.68 | 471 | 100 | 2 | A |
| 2b | 5.27 | 471 | 98.55 | 2 | B |

*A means the first isomer that elutes. B means the second isomer that elutes.

Optical Rotations

Optical rotations were measured on a Perkin-Elmer 341 polarimeter with a sodium lamp and reported as follows: $[\alpha]°$ (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ, (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 6

Optical Rotation data.

| Co. No. | $α_D$ (°) | Wavelength (nm) | Concentration w/v % | Solvent | Temp. (° C.) |
|---|---|---|---|---|---|
| 1a | +58.2 | 589 | 0.85 | DMF | 20 |
| 1b | −58.0 | 589 | 0.85 | DMF | 20 |
| 2a | +62.1 | 589 | 0.57 | DMF | 20 |
| 2b | −63.3 | 589 | 0.56 | DMF | 20 |

Nuclear Magnetic Resonance (NMR)

For a number of compounds, $^1$HNMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

TABLE 7

NMR.

| Co. No. | $^1$H NMR |
|---|---|
| 1 | (400 MHz, CDCl$_3$) δ ppm 0.28-0.40 (m, 2 H) 0.57-0.70 (m, 2 H) 1.11-1.23 (m, 1 H) 1.42 (t, J = 7.1 Hz, 3 H) 2.08-2.25 (m, 1 H) 2.42-2.55 (m, 1 H) 3.10 (d, J = 6.7 Hz, 2 H) 3.62-3.74 (m, 2 H) 3.90 (dq, J = 11.6, 3.8 Hz, 1 H) 4.00 (dd, J = 11.7, 7.7 Hz, 1 H) 4.13 (br. quin, J = 7.6 Hz, 1 H) 4.45 (q, J = 7.2 Hz, 2 H) 6.89 (d, J = 7.4 Hz, 1 H) 8.08 (s, 1 H) 8.10 (d, J = 7.4 Hz, 1 H). |
| 1a | (400 MHz, CDCl$_3$) δ ppm 0.28-0.41 (m, 2 H) 0.56-0.70 (m, 2 H) 1.10-1.23 (m, 1 H) 1.42 (t, J = 7.1 Hz, 3 H) 2.08-2.25 (m, 1 H) 2.42-2.54 (m, 1 H) 3.10 (d, J = 6.7 Hz, 2 H) 3.62-3.75 (m, 2 H) 3.90 (dq, J = 11.8, 4.2 Hz, 1 H) 4.00 (dd, J = 11.7, 7.7 Hz, 1 H) 4.13 (br. quin, J = 7.5 Hz, 1 H) 4.45 (q, J = 7.1 Hz, 2 H) 6.90 (d, J = 7.4 Hz, 1 H) 8.08 (s, 1 H) 8.10 (d, J = 7.4 Hz, 1 H). |
| 1b | (400 MHz, CDCl$_3$) δ ppm 0.27-0.41 (m, 2H) 0.56-0.70 (m, 2H) 1.11-1.23 (m, 1 H) 1.42 (t, J = 7.2 Hz, 3 H) 2.08-2.25 (m, 1 H) 2.42-2.55 (m, 1 H) 3.10 (d, J = 6.7 Hz, 2 H) 3.61-3.75 (m, 2 H) 3.90 (dq, J = 11.6, 3.9 Hz, 1 H) 4.00 (dd, J = 11.8, 7.9 Hz, 1 H) 4.13 (br. quin, J = 7.4 Hz, 1 H) 4.45 (q, J = 7.2 Hz, 2 H) 6.90 (d, J = 7.2 Hz, 1 H) 8.08 (s, 1 H) 8.10 (d, J = 7.4 Hz, 1 H). |
| 2 | (400 MHz, CDCl$_3$) δ ppm 1.21 (t, J = 6.9 Hz, 3 H) 1.36-1.48 (m, 3 H) 2.11-2.24 (m, 1 H) 2.43-2.56 (m, 1 H) 3.56 (q, J = 6.9 Hz, 2 H) 3.62-3.75 (m, 2 H) 3.90 (dq, J = 11.8, 4.2 Hz, 1 H) 4.00 (dd, J = 11.6, 7.6 Hz, 1 H) 4.14 (br. quin, J = 7.4 Hz, 1 H) 4.45 (q, J = 7.2 Hz, 2 H) 5.07 (s, 2 H) 6.93 (d, J = 7.4 Hz, 1 H) 8.08 (s, 1 H) 8.39 (d, J = 7.4 Hz, 1 H). |

Pharmacological Examples
A) In vitro Pharmacology

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I) are present. Compounds of Formula (I) are expected to have their effect substantially at mGluR2 by virtue of their ability to enhance the function of the receptor. The effects of positive allosteric modulators tested at mGluR2 using the [$^{35}$S]GTPγS binding assay method described below and which is suitable for the identification of such compounds, and more particularly the compounds according to Formula (I), are shown in Table 8.

[$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the positive allosteric modulation (PAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with a vortex and pipetting up and down. The suspension was centrifuged at 16,000 RPM (Sorvall RC-5C plus rotor SS-34) for 10 minutes and the supernatant discarded. The pellet was homogenized in 5 mM Tris-HCl, pH 7.4 using an ultra-turrax homogenizer and centrifuged again (18,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 μM GDP. Human mGlu2 receptor-containing membranes were thawed on ice and diluted in assay buffer supplemented with 14 µg/ml saponin. Membranes were pre-incubated with compound alone or together with a predefined (~$EC_{20}$) concentration of glutamate (PAM assay) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 µg of membrane protein in 10 mM HEPES acid, 10 mM HEPES salt, pH 7.4, 100 mM NaCl, 3 mM $MgCl_2$, 10 µM GDP and 2 µg/ml saponin. Total reaction volume was 200 µl. Reactions were terminated by rapid filtration through Unifilter-96 GF/B plates (Perkin Elmer, Massachusetts, USA) using a 96-well filtermate universal harvester. Filters were washed 6 times with ice-cold 10 mM $NaH_2PO_4$/10 mM $Na_2HPO_4$, pH 7.4. Filters were then air-dried, and 40 µl of liquid scintillation cocktail (Microscint-O) was added to each well. Membrane-bound radioactivity was counted in a Microplate Scintillation and Luminescence Counter from Perkin Elmer.

Data Analysis

The concentration-response curves of representative compounds of the present invention-obtained in the presence of $EC_{20}$ of mGluR2 agonist glutamate to determine positive allosteric modulation (PAM)—were generated using the Lexis software interface (developed at J&J). Data were calculated as % of the control glutamate response, defined as the maximal response that is generated upon addition of glutamate alone. Sigmoid concentration-response curves plotting these percentages versus the log concentration of the test compound were analyzed using non-linear regression analysis. The concentration producing half-maximal effect is then calculated as $EC_{50}$. The $pEC_{50}$ values below were calculated as the –log $EC_{50}$, when the $EC_{50}$ is expressed in M. $E_{max}$ is defined as relative maximal effect (i.e. maximal % effect relative to the control glutamate response).

Table 8 below shows the pharmacological data obtained for compounds of Formula (I).

TABLE 8

Pharmacological data for compounds according to the invention.

| Co. No. | GTPγS - hmGluR2 PAM $pEC_{50}$ | GTPγS - hmGluR2 PAM $E_{max}$ |
|---|---|---|
| 1 | 8.23 | 234.35 |
| 1a | 6.67 | 148.44 |
| 1b | 8.42 | 277.87 |
| 2 | 7.77 | 344.96 |
| 2a | 5.68 | 226.905 |
| 2b | 8.01 | 295.62 | n.c. means that the $pEC_{50}$ could not be calculated $pEC_{50}$ values were not calculated in cases where the concentration-response curve did not reach a plateau level.

All compounds were tested in presence of mGluR2 agonist glutamate at a predetermined $EC_{20}$ concentration, to determine positive allosteric modulation. $pEC_{50}$ values were calculated from a concentration-response experiment of at least 8 concentrations.

B) In vivo Pharmacology

Anticonvulsant Studies—6 Hz Test in Mice

At a predefined interval after drug treatment (standard: 0.5 h). individual mice were challenged with sufficient current (32 mA for 3 s; delivered through corneal electrodes) to elicit a limbic seizure. The manifestations of the "psychomotor" seizure were first described by Toman (Toman, J. E. P., 1951, "Neuropharmacologic considerations in psychic seizures" Neurology, 1, 444-460; Toman, J. E. P., Everett, G. M., Richards, R. K., 1952, "The search for new drugs against epilepsy" Tex. Rep. Biol. Med. 10, 96-104). We divide the behaviours into 4 observations: 1) Stun or immobility: The mouse may initially exhibit an appearance of having been "stunned". This may be characterized by immobility, or a lack of awareness regarding its environment as it goes directly into behaviours 2 and 3 (forepaw clonus or facial automatisms). The stun posture is most often upright, but the mouse may also fall on its side during a seizure; the fore limbs are often crossed and the hind limbs are spread wide apart. The "stunning" may occasionally be preceded by a few seconds of running with a rolling gait. 2) Forepaw clonus or automatism: usually resembles the mouse repeatedly raising its forepaw and then stomping it onto the ground. This is generally repeated several times, but must be repeated at least twice to be considered present. 3) Facial automatism: in the mouse best resembles jaw chomping or air biting; this also must occur at least twice to be considered present. 4) Elevated or Straub tail, which must be elevated to greater than a 45 degree angle to be considered present. The duration of the seizure varies from 5 to 75 s; at the end of the seizure, the animal rather suddenly resumes normal locomotion and exploratory behaviour. Each of the four above mentioned behaviours was scored as either absent (0) or present (1). Since control rats nearly always demonstrate at least 3 of the 4 behaviors, a score of 3 or 4 is a seizure and a score of 2 or less is considered protected.

TABLE 9

Anticonvulsant Studies - 6 Hz test in mice.

| | | Score ≤ 2 | | |
|---|---|---|---|---|
| Co. No. | Route | $ED_{50}$ (mg/kg) | $ED_{50}$ Low limit | $ED_{50}$ High limit |
| 1b | PO | 20 | 8.9 | 45 |
| | SC | 3.79 | 2.06 | 6.96 |
| 2b | PO | 20 | 8.9 | 45 |

$ED_{50}$ means median effective dose; PO means oral route; SC means subcutaneous route.

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I)

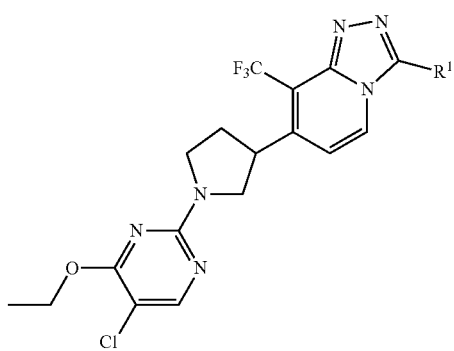

(I)

or a stereochemically isomeric form thereof, wherein $R^1$ is selected from $C_{1-6}$alkyl, $(C_{3-8}$cycloalkyl)$C_{1-3}$alkyl, and $(C_{1-3}$alkyloxy)$C_{1-3}$alkyl;

or a pharmaceutically acceptable salt thereof.

2. The compound according to claim 1, or a stereoisomeric form thereof, wherein $R^1$ is $(C_{3-8}$cycloalkyl)$C_{1-3}$alkyl, $(C_{1-3}$alkyloxy)$C_{1-3}$alkyl, and $C_{1-3}$alkyl.

3. The compound according to claim 1, wherein, $R^1$ is (cyclopropyl)methyl or (ethyloxy)methyl.

4. The compound according to claim 1, wherein the compound is selected from the group consisting of 7-[1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;

7-[(3*R)-1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;

7-[(3*S)-1-(5-chloro-4-ethoxy-pyrimidin-2-yl)pyrrolidin-3-yl]-3-(cyclopropylmethyl)-8-(trifluoromethyl)-[1,2,4]triazolo[4,3-a]pyridine;

7-[1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine;

7-[(3*R)-1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine; and 7-[(3*S)-1-(5-chloro-4-ethoxy-pyrimidin-2-yl)pyrrolidin-3-yl]-3-(ethoxymethyl)-8-(trifluoromethyl)-[1,2,4]triazolo[4,3-a]pyridine.

5. A pharmaceutical composition comprising a therapeutically effective amount of a compound according to claim 1 and a pharmaceutically acceptable carrier or excipient.

* * * * *